United States Patent [19]

Minetti

[11] Patent Number: 4,758,599
[45] Date of Patent: Jul. 19, 1988

[54] CLEAR, HYDROALCOHOLIC AFTERSHAVE LOTION WHICH MOISTURIZES, CONDITIONS, AND PREVENTS IRRITATION

[75] Inventor: Dawn C. Minetti, Clifton, N.J.

[73] Assignee: American Cyanamid Company, Stamford, Conn.

[21] Appl. No.: 870,485

[22] Filed: Jun. 4, 1986

[51] Int. Cl.$^4$ ............................ A61K 7/15; A61K 7/48
[52] U.S. Cl. ........................................ 514/844; 424/73; 424/195.1; 512/23; 512/5
[58] Field of Search ........................... 514/844; 424/73

[56]  References Cited

PUBLICATIONS

Janistyn, Reichstoffe, Seifen, Kosmetika, 1951, Bd. 2, p. 148-150, 152, & 185-189.
Bennett, The Cosmetic Formulary, 1937, pp. 36, 208 to 210.
The Merck Index, 1976, p. 846.

Primary Examiner—Dale R. Ore
Attorney, Agent, or Firm—C. J. Fickey

[57] ABSTRACT

A clear, hydroalcoholic solution that contains sodium lactate to moisturize, quaternium 26 to condition, contains chamomile as an anti-irritant with niacinamide to refresh the skin. This product provides extended protection against drying and is an improved topically applied base composition that provides enhanced refreshment and conditioning for personal care products.

2 Claims, No Drawings

CLEAR, HYDROALCOHOLIC AFTERSHAVE LOTION WHICH MOISTURIZES, CONDITIONS, AND PREVENTS IRRITATION

This invention relates to a hydroalcoholic composition which has a refreshing and conditioning effect on the skin. The invention more particularly relates to a hydroalcoholic composition which may be used to form the basis of different cosmetic compositions such as shave cream, moisturizing cream/lotion, afterbath splash, shampoo, hair conditioner, antiperspirant and splash-on lotion.

It is understood that the general function of an aftershave lotion is to relieve the discomfort and taut feeling of the skin caused by shaving. The purpose of an aftershave lotion is to soothe minor irritations, cool and refresh the skin and to give one an overall feeling of wellbeing. The most widely used form is that of an alcoholic solution.

The alcohol is generally the ingredient that gives a feeling of coolness and is refreshing. The alcohol also relieves the irritation and tension of the skin due to shaving, by acting as a mild astringent. Today's aftershave lotions usually contain 40%–60% alcohol. Higher concentrations than 60% cause excessive sting and smarting. When less than 40% alcohol is used, solubility problems arise with the perfume oil.

Small amounts of weak acids, e.g. benzoic acid (Mennen Skin Bracer) boric acid or lactic acid are used to neutralize the soap that is left on the skin from shaving. This helps to restore the normal acidity (10.11) of the skin.

Humectants are usually used up to a concentration of 3%. The most common are glycerol (Aqua Velva, English Leather, Aqua Velva Musk), propylene glycol (Mennen Skin Bracer, OLD SPICE ®, BLUE STRATOS ®, Brut, British Sterling, Hai Karate), polyethylene glycol and sorbitol. However, they do not soften the skin in the same manner as lipophilic emollients, which partially or completely occlude the skin surface.

Cationic quaternary ammonium salts may be used as antiseptics, at a level below 0.1%, along with 0.1% of a neutral or slightly acid salt of ethylenediamine tetraacetic acid, or a similar chelating agent. Those quats that are commonly used are benzalkonium chloride, cetyl trimethyl ammonium bromide, cetyl pyridinium chloride, disobutyl cresoxy ethoxy ethyl dimethyl benzyl ammonium chloride and N(acylcolaminoformylmethyl)pyridinium chloride. Halogenated phenolic antiseptics e.g. hexachlorophene, could be used in place of the quats.

There are products on the market that do not contain any ingredients other than alcohol, water and perfume (Jade East, Yardley of London Musk).

This invention goes beyond the historical use of an after-shave lotion. While it does cool, refresh and soothe the skin, it also provides extended protection against drying, enhanced conditioning and moisturizing of the skin, protects against infection, minor cuts and skin abrasions caused by shaving and nourishes and purifies the skin cells.

The invention is a composition comprising niacinamide, sodium lactate and quaternium 26 (a mink-aminopropyl dimethyl-2-hydroxyethyl ammonium chloride by Van Dyke and Co.).

The sodium lactate is a component of the stratum corneum. It is a naturally occurring humectant that is an extremely effective moisturizer. Sodium lactate is used in an amount of about 1 to 8%.

The quaternium 26 is an emollient that conditions the skin in the same manner as lipophilic emollients, by partially occluding the skin, yet, it is non-comedogenic i.e. it will not clog the pores and/or cause acne. The quaternium 26 also has antimicrobial activity against *Staphylococcus aureus, Escherichia coli, Pseudomonas aeruginosa, Candida albicans* and *Aspergillus niger.*

The niacinamide increases the blood flow, due to vasodilation of the peripheral blood vessels. This helps to quickly remove impurities from under the skin and to keep cells nourished. Niacinamide is used in an amount of about 0.25 to 2.5%.

This invention provides all of the historical functions of an ordinary after-shave lotion, while actually being good for your skin and perhaps even improving it. This composition also contains from 50% to 90% alcohol, without the associated sting and smarting. The quaternium 26 is utilized at about 0.5 to 8%, preferably 1.0% concentration for more conditioning and antimicrobial effect.

The ingredients being claimed i.e. sodium lactate, quaternium 26 and niacinamide may also be used as a combination, in a wide variety of personal care products.

For example, as previously mentioned, after-shave lotions, hand, face or body lotions or creams, shampoos or hair conditioners, soaps in liquified or solid forms, and the like.

The novel features and advantage of this invention lie in the unique ingredients-niacinamide, sodium lactate and quaternium 26, where each one alone has an advantage in and of itself. The niacinamide being the amide of niacin which is a vasodilator, aids in increasing the blood circulation, which speeds up the removal of any impurities that may be lying beneath the skin surface. The sodium lactate moisturizes the skin and promotes the retention of moisture. The quaternium 26 makes the skin soft and supple, reduces facial lipids, is non-comedogenic and exhibits antimicrobial activity against *Staphylococcus aureus, Escherichia coli, Pseudomonas aeruginosa, Candida albicans* and *Aspergillus niger.* Together, these ingredients refresh and condition the skin while providing the added benefit of protection against drying and irritation. This product offers enhanced conditioning benefits of personal care compositions, and perhaps even improves the condition of the skin.

The following specific Examples illustrate formulations of invention:

EXAMPLE I

| INGREDIENT | AMOUNT |
|---|---|
| Alcohol, SD-40 (94.9% by Volume) | 78.15000 |
| Menthol USP | 0.10000 |
| Quaternium 26 | 1.00000 |
| Chamomile Extract | 0.25000 |
| Aloe Vera Gel, Stabilized | 2.00000 |
| Sodium Lactate (60% Syrup) | 2.00000 |
| Niacinamide | 0.50000 |
| Water Deionized | 16.00000 |

EXAMPLE II

| INGREDIENT | AMOUNT |
|---|---|
| Alcohol, SD-40 (94.9% by Volume) | 78.65000 |

-continued

| INGREDIENT | AMOUNT |
| --- | --- |
| Menthol, USP | 0.10000 |
| Quaternium 26 | 1.00000 |
| Chamomile Extract | 0.25000 |
| Aloe Vera Gel, Stabilized | 2.00000 |
| Sodium Lactate (60% Syrup) | 2.00000 |
| Water, Deionized | 16.00000 |

EXAMPLE III

| INGREDIENT | AMOUNT |
| --- | --- |
| Alcohol, SD-40 (94.9% by Volume) | 81.15000 |
| Menthol, USP | 0.10000 |
| Chamomile Extract | 0.25000 |
| Aloe Vera Gel, Stabilized | 2.00000 |
| Niacinamide | 0.50000 |
| Water, Deionized | 16.00000 |

EXAMPLE IV

| INGREDIENT | AMOUNT |
| --- | --- |
| Alcohol, SD-40 (94.9% by Volume) | 81.65000 |
| Menthol, USP | 0.10000 |
| Chamomile Extract | 0.25000 |
| Aloe Vera Gel, Stabilized | 2.00000 |
| Water, Deionized | 16.00000 |

EXAMPLE V

| INGREDIENT | WEIGHT % |
| --- | --- |
| Alcohol SD-40, 190 Proof | 75.35 |
| Perfume 75398 | 2.00 |
| Menthol | 0.10 |
| Ceraphyl 65 | 1.00 |
| Chamomile Extract | 0.25 |
| Aloe Vera Stabilized | 2.00 |
| Sodium Lactate | 2.00 |
| Niacinamide | 0.50 |
| Deionized Water | 16.00 |
| FD & C Yellow 5 (1.0% soln.) | 0.50 |
| FD & C Blue 1 (1.0% soln.) | 0.30 |

EXAMPLE VI

| INGREDIENTS | WEIGHT % |
| --- | --- |
| Alcohol SD-40, 190 Proof | 74.10 |
| Cremophor RH40 | 1.00 |
| Vitamin E | 0.50 |
| Perfume 75398 | 2.00 |
| Menthol | 0.10 |
| Ceraphyl 65 | 1.00 |
| Sodium Lactate | 2.00 |
| Aloe Vera, Stabilized | 2.00 |
| Chamomile Extract | 0.50 |
| Niacinamide | 0.50 |
| Deionized Water | 15.50 |
| FD & C Yellow 5 (1.0% soln.) | 0.50 |
| FD & C Blue 1 (1.0% soln.) | 0.30 |

EXAMPLE VII

| INGREDIENT | AMOUNT |
| --- | --- |
| Alcohol, SD-40 (94.9% by Volume) | 79.15000 |
| Menthol, USP | 0.10000 |
| Chamomile Extract | 0.25000 |
| Aloe Vera Gel, Stabilized | 2.00000 |
| Sodium Lactate (60% Syrup) | 2.00000 |
| Niacinamide | 0.50000 |
| Water, Deionized | 16.00000 |

EXAMPLE VIII

| INGREDIENT | AMOUNT |
| --- | --- |
| Alcohol, SD-40 (94.9% by Volume) | 80.15000 |
| Menthol, USP | 0.10000 |
| Quaternium 26 | 1.00000 |
| Chamomile Extract | 0.25000 |
| Aloe Vera Gel, Stabilized | 2.00000 |
| Niacinamide | 0.50000 |
| Water, Deionized | 16.00000 |

EXAMPLE IX

| INGREDIENT | AMOUNT |
| --- | --- |
| Alcohol, SD-40 (94.9% by Volume) | 80.65000 |
| Menthol, USP | 0.10000 |
| Quaternium 26 | 1.00000 |
| Chamomile Extract | 0.25000 |
| Aloe Vera Gel, Stabilized | 2.00000 |
| Water, Deionized | 16.00000 |

EXAMPLE X

| INGREDIENT | AMOUNT |
| --- | --- |
| Alcohol, SD-40 (94.9% by Volume) | 79.65000 |
| Menthol, USP | 0.10000 |
| Chamomile Extract | 0.25000 |
| Aloe Vera Gel, Stabilized | 2.00000 |
| Sodium Lactate (60% Syrup) | 2.00000 |
| Water, Deionized | 16.00000 |

EXAMPLE XI

Tests were conducted to illustrate the effectiveness of the inventive composition on human skin. Testing was intended to prove: (1) conditioning, (2) moisturization, and (3) overall improvement of skin.

METHODOLOGY

CLINICAL PROTOCOL-Forearm Skin Moisturization Test

1. Male subjects reported to the PEC and 5 sites of one square inch each were marked with ink on each interior forearm, roughly from the wrist to the elbow.
2. A dermatometer reading was taken on each of the ten sites, designated "baseline".
3. One drop of each product was applied per site (nothing if untreated) and spread over the site with a gloved finger.
4. After one minute, another dermatometer reading was taken on each site, designated "initial".
5. Dermatometer readings were taken, 1, 2 and 3 hours after the intial reading.

STATISTICAL ANALYSIS

1. Dermatometer readings at 0 (initial), 1, 2 and 3 hours post-treatment were corrected for baseline by subtracting the baseline results.

2. The treatment and time effects were estimated using analysis of variance and regression analysis, which corrected for the effects of sites.

RESULTS:

Preliminary analysis showed that skin moisture increased in a linear gradient from wrist (lowest) to elbow (highest) on the forearm sites, and these differences were statistically significant (p 0.0001). This justified the statistical design which balanced treatments over sites, and also justified the subsequent statistical analysis, which corrected for site effect.

The dermatometer readings after treatment application increased about 13 units over the baseline reading (averaged over sites and treatments). The readings then fell significantly below baseline at one hour, and leveled out thereafter (at two and three hours). Since high ambient humidity conditions prevailed during test, this effect may be attributable to the skin equilibrating with the lower humidity in the PEC.

Differences among treatments were significant only immediately after treatment application. No differences were seen among treatments at 1, 2 or 3 hours post treatment. For time zero, the moisture increases over baseline are shown below along with grouping of treatments not significantly different at p=0.05.

| PRODUCT | ACTIVES (Presence or Absence) | | | MOISTURE INCREASES OVER BASELINE @ | PRODUCT GROUPING* |
|---|---|---|---|---|---|
| | CERAPHYL | LACTATE | LIACIN | | |
| I | (Mennen) | | | 22.0 | a |
| A | + | + | + | 19.1 | a,b |
| D | + | + | 0 | 16.6 | a,b,c |
| E | + | 0 | 0 | 14.7 | a,b,c,d |
| C | + | 0 | + | 13.3 | b,c,d,e |
| F | 0 | + | 0 | 12.9 | b,c,d,e |
| B | 0 | + | + | 9.5 | c,d,e |
| G | 0 | 0 | + | 8.1 | d,e |
| J | (Untreated) | | | 6.5 | d,e |
| H | 0 | 0 | 0 | 5.6 | e |

@ Dermatometer Units
*Products with similar letters are not significantly different at p = 0.05.

As can be seen above, high moisturization was correlated with the presence of Ceraphyl and, to a lesser extent, with sodium lactate. The average effect of Ceraphyl was 6.8 dermatometer units (p=0.0002) and the average effect of sodium lactate was 4.5 dermatometer units (p=0.0158), and these effects were additive.

I claim:

1. An aftershave composition having skin conditioning action, said composition comprising from 50 to 90% of a lower alcohol, 0.25 to 2.5% niacinamide, 1.0 to 8.0% sodium lactate, 0.5 to 8.0 quaternuim 26 and 0 to 50% water.

2. The composition of claim 1 containing in addition a fragrance.

* * * * *